(12) United States Patent
Hopkins et al.

(10) Patent No.: US 8,044,059 B2
(45) Date of Patent: Oct. 25, 2011

(54) STABLE EMULSIFIABLE CONCENTRATE FORMULATION

(75) Inventors: Derek J. Hopkins, New Plymouth (NZ); Robert Matthew Buttimor, Spotswood (NZ)

(73) Assignee: Dow AgroSciences LLC, Indianapolis, IN (US)

( * ) Notice: Subject to any disclaimer, the term of this patent is extended or adjusted under 35 U.S.C. 154(b) by 490 days.

(21) Appl. No.: 12/389,481

(22) Filed: Feb. 20, 2009

(65) Prior Publication Data
US 2009/0215797 A1    Aug. 27, 2009

Related U.S. Application Data

(60) Provisional application No. 61/067,127, filed on Feb. 26, 2008.

(51) Int. Cl.
*A01N 43/90* (2006.01)
*A01N 37/10* (2006.01)
*A01N 43/40* (2006.01)
*A01P 13/00* (2006.01)

(52) U.S. Cl. ............... 514/259.1; 514/345; 514/349; 514/354; 514/568

(58) Field of Classification Search ............ 514/259.31, 514/345, 349, 354, 568
See application file for complete search history.

(56) References Cited

U.S. PATENT DOCUMENTS

| 2008/0004182 A1 | 1/2008 | Linton et al. |
| 2009/0054239 A1 | 2/2009 | Hopkins |

FOREIGN PATENT DOCUMENTS

WO    WO2007/140332    12/2007

OTHER PUBLICATIONS

Dow AgroSciences Ltd. Invoice 27 / 43613493 for order of GALAXY Herbicide 4X5L Bottles sent to Masstock Arable Ltd. dated Mar. 5, 2007.

*Primary Examiner* — Raymond Henley, III
(74) *Attorney, Agent, or Firm* — Craig E. Mixan

(57) ABSTRACT

The use of an N,N-dimethyl alkylamide or an N-alkanoyl morpholine provides a stable emulsifiable concentrate composition that hinders de-esterification and transesterification of mixtures of a carboxylic acid herbicide and an ester of a different carboxylic acid herbicide. The N,N-dimethyl alkylamide or N-alkanoyl morpholine additionally stabilizes emulsifiable concentrates containing a triazolopyrimidine herbicide having at least one methoxy group on the triazolopyrimidine ring.

10 Claims, No Drawings

US 8,044,059 B2

STABLE EMULSIFIABLE CONCENTRATE FORMULATION

FIELD OF THE INVENTION

This invention concerns the use of an N,N-dimethyl alkyl amide or an N-alkanoyl morpholine to provide a stable emulsifiable concentrate composition that hinders de-esterification and transesterification of mixtures of a carboxylic acid herbicide and an ester of a different carboxylic acid herbicide. The N,N-dimethyl alkyl amide or N-alkanoyl morpholine may additionally stabilize emulsifiable concentrates containing a triazolopyrimidine herbicide having at least one methoxy group on the triazolopyrimidine ring.

BACKGROUND OF THE INVENTION

To design an agricultural formulation product, the most important question to be answered is its stability. Failure to meet a set of stability requirements which usually depends on the specific market, application and regulations will certainly lead to failure of its commercialization. There are many causes of formulation instabilities, such as a) chemical instabilities due to reactions between ingredients (actives and/or inerts, etc.), photo-degradations, and oxidations, etc., b) physical instabilities due to phase separations (Ostwald ripening, crystallization, sedimentation or creaming etc.) and c) environmental factors (temperature, humidity/moisture, etc.). In today's agrichemical market, it becomes increasingly common to design formulations to contain multiple active ingredients and their required solvents, safeners, and/or adjuvants, etc., in order to achieve the optimal spectrum, efficacy, and delivery efficiency, which consequently makes formulation stability more and more challenging. Therefore, technologies that can effectively isolate, hinder, or eliminate, adverse reactions or interactions between incompatible ingredients are often critical for a successful product.

The emulsifiable concentrate (EC) is one of the most common formulation types for many agricultural products, where mixtures of oil soluble active ingredients and emulsifying agents (surfactants) are dissolved in an organic solvent. The emulsifying agent enables the EC to disperse easily in water, thereby forming a "milky" and homogenous emulsion. Emulsifiable concentrates are generally easy to mix and do not settle out quickly when agitation is stopped, are relatively easy to handle, transport and store, are not abrasive to spray equipment and do not clog spray screens and nozzles and are easy to manufacture. However, many challenges may exist, particularly when a carboxylic acid herbicide is mixed with an ester of a different carboxylic acid herbicide. For example, a composition containing fluoroxypyr meptyl ester and clopyralid free acid has been found to be extremely useful because of the complimentary spectrum of weed control of the individual components. However, in typical emulsifiable concentrate formulations, transesterification to clopyralid meptyl ester and fluoroxypyr free acid can occur. This is problematic from a regulatory perspective because both the free acid and particular ester of both the active herbicidal ingredients may not be registered. Thus it would be desirable to retard such transesterification within the formulation.

In addition, when a triazolopyrimidine herbicide having at least one methoxy group on the triazolopyrimidine ring like florasulam, N-(2,6-difluorophenyl)-8-fluoro-5-methoxy[1,2,4]triazolo[1,5-c]pyrimidine-2-sulfonamide, is incorporated into an emulsifiable concentrate, particularly in admixture with a carboxylic acid herbicide and/or an ester of a carboxylic acid herbicide, it often is degraded to the herbicidally inactive hydroxy analog. Similarly, it would be desirable to prevent such degradation within the formulation.

SUMMARY OF THE INVENTION

It has now been found that N,N-dimethyl alkyl amides and N-alkanoyl morpholine both prevent the transesterification of mixtures of a carboxylic acid herbicide and an ester of a different carboxylic acid herbicide and the degradation of a triazolopyrimidine herbicide having at least one methoxy group on the triazolopyrimidine ring, such as florasulam, in emulsifiable concentrates.

The present invention concerns a method to provide a stable emulsifiable concentrate composition containing a mixture of a carboxylic acid herbicide and an ester of a different carboxylic acid herbicide by hindering de-esterification and transesterification which comprises incorporating into the composition from about 10 to about 600 grams/liter (g/L) of an N,N-dimethyl ($C_6$-$C_{12}$)alkyl amide or an N($C_5$-$C_{11}$)alkanoyl morpholine.

Another aspect of the present invention concerns a method to provide a stable emulsifiable concentrate composition containing a triazolopyrimidine herbicide having at least one methoxy group on the triazolopyrimidine ring in admixture with a carboxylic acid herbicide and/or an ester of a carboxylic acid herbicide by hindering degradation of the methoxy group to an hydroxy group which comprises incorporating into the composition from about 10 to about 600 g/L of an N,N-dimethyl ($C_6$-$C_{12}$)alkyl amide or an N—($C_5$-$C_{11}$)alkanoyl morpholine.

Another aspect of the invention concerns a stable emulsifiable concentrate composition comprising a) from about 5 to about 500 g/L of a carboxylic acid herbicide as a free acid, b) from about 10 to about 700 g/L of a different carboxylic acid herbicide as an ester, c) from about 10 to about 600 g/L of an N,N-dimethyl ($C_6$-$C_{12}$)alkyl amide or an N—($C_5$-$C_{11}$)alkanoyl morpholine, and d) from about 60 to about 720 g/L of an organic solvent and surfactants.

Another aspect of the invention concerns a stable emulsifiable concentrate composition comprising a) from about 1 to about 5 g/L of a triazolopyrimidine herbicide having at least one methoxy group on the triazolopyrimidine ring, b) from about 5 to about 700 g/L of a carboxylic acid herbicide and/or an ester of a carboxylic acid herbicide, c) from about 10 to about 600 g/L of an N,N-dimethyl ($C_6$-$C_{12}$)alkyl amide or an N—($C_5$-$C_{11}$)alkanoyl morpholine, and d) from about 60 to about 720 g/L of an organic solvent and surfactants.

DETAILED DESCRIPTION OF THE INVENTION

This invention provides stable emulsifiable concentrate compositions that contain a mixture of a carboxylic acid herbicide and an ester of a different carboxylic acid herbicide or contain a triazolopyrimidine herbicide having at least one methoxy group on the triazolopyrimidine ring in admixture with a carboxylic acid herbicide and/or an ester of a carboxylic acid herbicide.

By a carboxylic acid herbicide is meant an herbicide that contains a carboxylic acid functionality. This functionality can be present as a free acid COOH) or an ester (COOR[1] wherein R[1] represents a $C_1$-$C_8$ alkyl group, a $C_3$-$C_8$ alkenyl group, a $C_3$-$C_8$ alkynyl group or a $C_3$-$C_8$ alkoxyalkyl group). Herbicidal carboxylic acids include, but are not limited to: benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; and pyridinyloxyacetic herbicides such as fluoroxypyr and triclopyr. Preferred carboxylic acid herbicides are 2,4-D, MCPA, dicamba, clopyralid, fluoroxypyr and triclopyr.

Triazolopyrimidine herbicides having at least one methoxy group on the triazolopyrimidine ring include, but are not limited to, florasulam, N-(2,6-difluorophenyl)-8-fluoro-5-methoxy[1,2,4]triazolo[1,5-c]pyrimidine-2-sulfonamide; penoxsulam, 2-(2,2-difluoroethoxy)-N-(5,8-dimethoxy[1,2,4]triazolo[1,5-c]pyrimidin-2-yl)-6-(trifluoromethyl)benzenesulfonamide; and pyroxsulam, N-(5,7-dimethoxy[1,2,4]-triazolo[1,5-a]pyrimidin-2-yl)-2-methoxy-4-(trifluoromethyl)-3-pyridinesulfonamide.

The term "alkyl", as used herein, includes within its scope straight chain, branched chain and cyclic moieties.

N,N-Dimethyl ($C_6$-$C_{12}$) alkylamides are commercially available under various tradenames including, for example, Agnique AMD 810 (Cognis Inc.) or Genagen 4166 (Clariant GmbH), and are often supplied as mixtures such as N,N-dimethyloctanamide/decanamide. N—($C_5$-$C_{11}$) Alkanoyl morpholines have the structural formula:

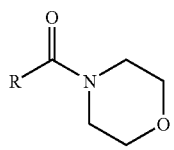

wherein R is a $C_5$-$C_{11}$ alkyl group
and are commercially available as Jeffsol AG1730 (Huntsman Corporation; mixture of N-alkanoyl morpholines from N-pentanoylmorpholine to N-undecanoyl-morpholine). The N,N-dimethyl ($C_6$-$C_{12}$)alkylamide or the N—($C_5$-$C_{11}$)alkanoyl morpholine is usually present at a concentration from about 10 g/L to about 600 g/L.

The organic solvents typically used in the stable emulsifiable concentrate compositions of the present invention include, but are not limited to, petroleum fractions or hydrocarbons such as mineral oil, aromatic solvents, xylene, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like; esters of mono, di and polycarboxylic acids and the like. The solvent is usually present at a concentration of from about 0 g/L to about 600 g/L.

The surfactants typically used in the stable emulsifiable concentrate compositions of the present invention can be anionic, cationic or nonionic in character. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surfactants include salts of alkyl sulfates, such as diethanolammonium lauryl sulfate; alkylarylsulfonate salts, such as calcium dodecylbenzenesulfonate; alkyl and/or arylalkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; and mixtures thereof. The surfactant or mixture of surfactants is usually present at a concentration of from about 60 g/L to about 120 g/L.

In addition to the compositions and uses set forth above, the present invention also embraces the composition and use of these emulsifiable concentrates in combination with one or more additional compatible ingredients. Other additional ingredients may include, for example, one or more other pesticides, dyes, and any other additional ingredients providing functional utility, such as, for example, stabilizers, fragrants, viscosity-modifying additives, suspension aids, dispersants, and freeze-point depressants.

The following examples illustrate the present invention.
Description of Products Used in the Examples

| Component | Description | Supplier |
|---|---|---|
| Tensiofix N9811HF | Proprietary surfactant blend | Omnichem |
| Tensiofix N9824HF | Proprietary surfactant blend | Omnichem |
| Tensiofix N9839HF | Proprietary surfactant blend | Omnichem |
| Agrimul Lipo D | Proprietary surfactant blend | Cognis |
| Agrimul Hydro D | Proprietary surfactant blend | Cognis |
| Agrimul Block D | Proprietary surfactant blend | Cognis |
| Biosoft N-411 | Isopropylamine salt of dodecylbenzene sulfonic acid | Stepan |
| Toximul 8320 | Copolymer butanol EO/PO | Stepan |
| Agnique CSO 40 | Castor oil with 40 moles EO | Cognis |
| Genagen 4166 | Mixture of N,N-dimethyl octanamide/decanamide | Clariant |
| Jeffsol AG1730 | N-alkyl($C_6$-$C_{12}$)noylmorpholine | Huntsman |
| Solvesso 100 | Aromatic hydrocarbon fluid | ExxonMobil |
| Solvesso 150ND | Aromatic hydrocarbon fluid | ExxonMobil |
| Solvesso 200ND | Aromatic hydrocarbon fluid | ExxonMobil |

Compositions according to the invention were prepared with the following general procedure:

The carboxylic acid herbicide and N,N-dimethyl alkyl amide or N-alkanoyl morpholine solvent were combined to form a solution. Optionally, a triazolo-pyrimidine herbicide having at least one methoxy group on the triazolopyrimidine ring is also added at this stage and mixed until a clear solution obtained. The second solvent, if used and the ester of the different carboxylic acid herbicide along with emulsifiers were combined with the solution to obtain the finished product. Samples were then stored for 1 week at −10° C. with seeding to assess cold temperature solubility and 2 weeks at 54° C. to determine stability of the active ingredients.

Examples 1 to 4

The following compositions, using a N,N-dimethyl alkyl amide solvent all formed clear solutions with no sign of phase separation on storage at −10° C. for 1 week and remained free of transesterification as exhibited by greater than 95% retention of each active ingredient after storage at 54° C. for 2 weeks.

|  | Concentration/g/L | | | |
| --- | --- | --- | --- | --- |
|  | Example 1 | Example 2 | Example 3 | Example 4 |
| Clopyralid acid | 50.0 | 60.0 | 23.3 | 30.0 |
| Triclopyr Butotyl | 139.1 | 333.8 | — | — |
| Fluroxypyr Meptyl | 108.1 | — | 86.5 | 144.0 |
| MCPA 2EHE | — | — | 416.1 | — |
| Ioxynil Octanoate | — | — | — | 161.0 |
| Tensiofix N9811HF | 15.9 | 43.43 | — | — |
| Tensiofix N9839HF | 63.8 | 28.95 | 20.0 | — |
| Tensiofix N9824HF | — | — | 40.0 | — |
| Agrimul Lipo D | — | — | — | 22.0 |
| Agrimul Hydro D | — | — | — | 78.5 |
| Propylene glycol | 20.0 | — | — | — |
| Genagen 4166 | 75.0 | 90.0 | 35.0 | 45.0 |
| Solvesso 100 | To 1 liter | To 1 liter | To 1 liter | To 1 liter |

Examples 1 to 4 active ingredient storage stability results:

|  | Active Ingredient | Concentration Initial/% w/w | Concentration after 2 weeks at 54° C./% w/w | Retention of Active Ingredient after Storage/% |
| --- | --- | --- | --- | --- |
| 1 | Clopyralid acid | 4.8 | 4.8 | 100.0 |
|  | Triclopyr-butotyl | 13.9 | 13.8 | 99.3 |
|  | Fluroxypyr-meptyl | 10.9 | 11.2 | 102.8 |
| 2 | Clopyralid acid | 5.5 | 5.6 | 101.8 |
|  | Triclopyr-butotyl | 32.8 | 31.9 | 97.3 |
| 3 | Clopyralid acid | 2.3 | 2.3 | 100.0 |
|  | Fluroxypyr-meptyl | 8.6 | 8.6 | 100.0 |
|  | MCPA 2-ethylhexyl | 41.0 | 40.4 | 98.5 |
| 4 | Clopyralid acid | 2.9 | 2.9 | 100.0 |
|  | Fluroxypyr-meptyl | 14.3 | 14.1 | 98.6 |
|  | Ioxynil-octanoate | 15.7 | 16.1 | 102.5 |

Examples 5 to 8

The following compositions, using an N-alkanoyl morpholine solvent all formed clear solutions with no sign of phase separation on storage at −10° C. for 1 week and remained free of de-esterification and transesterification as exhibited by greater than 95% retention of each active ingredient after storage at 54° C. for 2 weeks.

|  | Concentration/g/L | | | |
| --- | --- | --- | --- | --- |
|  | Example 5 | Example 6 | Example 7 | Example 8 |
| Clopyralid acid | 50.0 | 60.0 | 23.3 | 30.0 |
| Triclopyr Butotyl | 139.1 | 333.8 | — | — |
| Fluroxypyr Meptyl | 108.1 | — | 86.5 | 144.0 |
| MCPA 2EHE | — | — | 416.1 | — |
| Ioxynil Octanoate | — | — | — | 161.0 |
| Tensiofix N9811HF | 15.9 | 43.43 | — | — |
| Tensiofix N9839HF | 63.8 | 28.95 | 20.0 | — |
| Tensiofix N9824HF | — | — | 40.0 | — |
| Agrimul Lipo D | — | — | — | 22.0 |
| Agrimul Hydro D | — | — | — | 78.5 |
| Propylene glycol | 20.0 | — | — | — |
| Jeffsol AG1730 | 75.0 | 90.0 | 35.0 | 45.0 |
| Solvesso 100 | To 1 liter | To 1 liter | To 1 liter | To 1 liter |

Examples 5 to 8 active ingredient storage stability results:

|  | Active Ingredient | Concentration Initial/% w/w | Concentration after 2 weeks at 54° C./% w/w | Retention of Active Ingredient after Storage/% |
| --- | --- | --- | --- | --- |
| 5 | clopyralid acid | 4.98 | 4.93 | 99.0 |
|  | triclopyr-butotyl | 14.27 | 13.58 | 95.2 |
|  | fluroxypyr-meptyl | 10.88 | 10.79 | 99.2 |
| 6 | clopyralid acid | 5.93 | 5.88 | 99.2 |
|  | triclopyr-butotyl | 32.97 | 31.55 | 95.7 |
| 7 | clopyralid acid | 2.38 | 2.30 | 96.6 |
|  | fluroxypyr-meptyl | 8.79 | 8.59 | 97.7 |
|  | MCPA 2-ethylhexyl | 40.80 | 39.86 | 97.7 |
| 8 | clopyralid acid | 2.96 | 2.96 | 100.0 |
|  | fluroxypyr-meptyl | 1.36 | 1.35 | 99.3 |
|  | ioxynil-octanoate | 15.97 | 16.05 | 100.5 |

Comparisons 1 to 4

Compositions corresponding to those of Examples 1 to 8 were prepared without the addition of an N,N-dimethyl alkyl amide or N-alkanoyl morpholine solvent (directly substituted with N-methyl-2-pyrrolidone solvent) and stored for 1 week at −10° C. and 2 weeks at 54° C. All four compositions remained free of phase separation but with less than 95% retention of active ingredients after storage indicated de-esterification and transesterification between the carboxylic acid and ester herbicides.

Comparisons 1 to 4 active ingredient storage stability results:

|  | Active Ingredient | Concentration Initial/% w/w | Concentration after 2 weeks at 54° C./% w/w | Retention of Active Ingredient after Storage/% |
| --- | --- | --- | --- | --- |
| 1 | clopyralid acid | 5.21 | 5.22 | 100.2 |
|  | triclopyr-butotyl | 13.81 | 12.12 | 87.7 |
|  | fluroxypyr-meptyl | 10.86 | 10.47 | 96.4 |
| 2 | clopyralid acid | 6.20 | 6.17 | 99.5 |
|  | triclopyr-butotyl | 32.33 | 28.94 | 89.5 |
| 3 | clopyralid acid | 2.46 | 2.30 | 93.5 |
|  | fluroxypyr-meptyl | 8.63 | 8.44 | 97.8 |
|  | MCPA 2-ethylhexyl | 40.56 | 38.50 | 94.9 |
| 4 | clopyralid acid | 3.04 | 3.03 | 99.7 |
|  | fluroxypyr-meptyl | 1.39 | 1.31 | 94.2 |
|  | ioxynil-octanoate | 16.11 | 16.08 | 99.8 |

Example 9

This example illustrates the beneficial effect of adding an N,N-dimethyl alkyl amide solvent to solutions of a carboxylic acid herbicide with an ester of a carboxylic acid herbicide optionally containing florasulam. Formulation prepared and tested using the general method of Examples 1 to 4 according to the following composition:

|  | Concentration/g/L Example 9 |
|---|---|
| Clopyralid acid | 80.0 |
| Fluroxypyr meptyl | 144.0 |
| Florasulam | 2.5 |
| Agrimul Hydro D | 60.0 |
| Agrimul Block D | 40.0 |
| Genagen 4166 | 200.0 |
| Solvesso 200ND | To 1 liter |

The composition formed a clear solution with no sign of phase separation on storage at −10° C. for 1 week and remained free of transesterification and decomposition as exhibited by greater than 95% retention of each active ingredient after storage at 54° C. for 2 weeks.

Example 9 active ingredient storage stability results:

|  | Concentration Initial/% w/w | Concentration after 2 weeks at 54° C./% w/w | Retention of Active Ingredient after Storage/% |
|---|---|---|---|
| Clopyralid acid | 7.7 | 7.6 | 98.7 |
| Fluroxypyr-meptyl | 13.3 | 12.9 | 97.0 |
| Florasulam | 0.25 | 0.25 | 100.0 |

Comparisons 5 to 9

Compositions corresponding to those of Example 9 were prepared without the addition of the N,N-dimethyl alkyl amide solvent and stored for 1 week at −10° C. and 2 weeks at 54° C. All five compositions remained free of phase separation but with less than 95% retention of each active ingredient after storage indicated de-esterification and transesterification between the carboxylic acid and ester herbicides and decomposition of florasulam.

|  | Concentration/g/L | | | | |
|---|---|---|---|---|---|
| Comparison | 5 | 6 | 7 | 8 | 9 |
| Clopyralid acid | 80.0 | 80.0 | 80.0 | 80.0 | 80.0 |
| Fluroxypyr meptyl | 144.0 | 144.0 | 144.0 | 144.0 | 144.0 |
| Florasulam | 2.5 | 2.5 | 2.5 | 2.5 | 2.5 |
| Agrimul Hydro D | 90.0 | 60.0 | 60.0 | 60.0 | 60.0 |
| Agrimul Block D | 10.0 | 40.0 | 40.0 | 40.0 | 40.0 |
| γ-butrolactone | 450.0 | — | — | — | — |
| Sulfolane | — | 200.0 | — | — | — |
| Tetrahydrofurfuryl alcohol | — | — | 200.0 | — | — |
| Benzoyl alcohol | — | — | — | 200.0 | — |
| α-terpineol | — | — | — | — | 200.0 |
| Solvesso 150ND | To 1 Liter | — | — | — | — |
| Solvesso 200ND | — | To 1 Liter | To 1 Liter | To 1 Liter | To 1 Liter |

Comparisons 5 to 9 active ingredient storage stability results:

|  | Active Ingredient | Concentration Initial/% w/w | Concentration after 2 weeks at 54° C./% w/w | Retention of Active Ingredient after Storage/% |
|---|---|---|---|---|
| 5 | Clopyralid acid | 7.70 | 7.12 | 92.5 |
|  | Fluroxypyr-meptyl | 13.52 | 12.35 | 91.3 |
|  | Florasulam | 0.23 | 0.20 | 87.0 |
| 6 | Clopyralid acid | 7.73 | 6.81 | 88.1 |
|  | Fluroxypyr-meptyl | 14.15 | 13.02 | 92.0 |
|  | Florasulam | 0.24 | 0.19 | 79.2 |
| 7 | Clopyralid acid | 7.47 | 5.67 | 75.9 |
|  | Fluroxypyr-meptyl | 13.98 | 12.45 | 89.1 |
|  | Florasulam | 0.24 | 0.20 | 83.3 |
| 8 | Clopyralid acid | 7.20 | 3.29 | 45.7 |
|  | Fluroxypyr-meptyl | 13.80 | 8.94 | 64.8 |
|  | Florasulam | 0.28 | 0.14 | 50.0 |
| 9 | Clopyralid acid | 7.68 | 7.10 | 92.4 |
|  | Fluroxypyr-meptyl | 14.27 | 12.35 | 86.4 |
|  | Florasulam | 0.24 | 0.23 | 95.8 |

Examples 10 and 11

These examples illustrate the beneficial effect of adding N,N-dimethyl alkyl amide solvent to solutions of a phenoxy acid, florasulam and optionally an ester of a different carboxylic acid herbicide. Formulations prepared and tested using the general method of Examples 1 to 4 according to the following compositions:

|  | Concentration/g/L | |
|---|---|---|
|  | Example 10 | Example 11 |
| 2,4-D acid | 420.0 | 320.0 |
| Florasulam | 3.8 | 3.3 |
| Fluroxypyr-meptyl | — | 46.8 |
| BioSoft N-411 | 120.0 | 120.0 |
| Agnique CSO 40 | 40.0 | 40.0 |
| Toximul 8320 | 40.0 | 40.0 |
| Solvesso 200ND | 45.0 | 50.0 |
| Genagen 4166 | To 1 liter | To 1 liter |

The composition formed a clear solution with no sign of phase separation on storage at −10° C. for 1 week and remained free of transesterification and decomposition as exhibited by greater than 95% retention of each active ingredient after storage at 54° C. for 2 weeks.

Examples 10 and 11 active ingredient storage stability results:

|  | Active Ingredient | Concentration Initial/% w/w | Concentration after 2 weeks at 54° C./% w/w | Retention of Active Ingredient after Storage/% |
|---|---|---|---|---|
| 10 | 2,4-D acid | 38.90 | 38.00 | 97.7 |
|  | Florasulam | 0.29 | 0.29 | 100.0 |
| 11 | 2,4-D acid | 30.40 | 29.90 | 98.4 |
|  | Florasulam | 0.31 | 0.30 | 96.8 |
|  | Fluroxypyr-meptyl | 4.54 | 4.39 | 96.7 |

Comparisons 10 to 13

Compositions corresponding to those of Examples 10 and 11 were prepared without the addition of the N,N-dimethyl alkyl amide solvent and stored for 1 week at −10° C. and 2 weeks at 54° C.

| | Concentration/g/L | | | |
|---|---|---|---|---|
| | Comparison 10 | Comparison 11 | Comparison 12 | Comparison 13 |
| 2,4-D acid | 420.0 | 420.0 | 320.0 | 320.0 |
| Florasulam | 3.8 | 3.8 | 3.3 | 3.3 |
| Fluroxypyr-meptyl | — | — | 46.8 | 46.8 |
| BioSoft N-411 | 120.0 | 120.0 | 120.0 | 120.0 |
| Agnique CSO 40 | 40.0 | 40.0 | 40.0 | 40.0 |
| Toximul 8320 | 40.0 | 40.0 | 40.0 | 40.0 |
| Solvesso 200ND | 45.0 | 45.0 | 50.0 | 50.0 |
| Tetrahydrofurfuryl alcohol | To 1 liter | — | To 1 liter | — |
| Diethylene glycol monoethyl ether | | To 1 liter | | To 1 liter |

Both compositions remained free of phase separation but with less than 95% retention of each active ingredient after storage indicated possible esterification of the phenoxy acid with the coformulants and decomposition of florasulam. Comparisons 10 to 13 active ingredient storage stability results:

| | Active Ingredient | Concentration Initial/% w/w | Concentration after 2 weeks at 54° C./% w/w | Retention of Active Ingredient after Storage/% |
|---|---|---|---|---|
| 10 | 2,4-D acid | 33.69 | 19.53 | 58.0 |
| | Florasulam | 0.32 | 0.26 | 81.3 |
| 11 | 2,4-D acid | 33.68 | 20.32 | 60.3 |
| | Florasulam | 0.34 | 0.28 | 82.4 |
| 12 | 2,4-D acid | 27.97 | 16.35 | 58.5 |
| | Florasulam | 0.28 | 0.21 | 75.0 |
| | Fluroxypyr-meptyl | 4.05 | 3.87 | 95.6 |
| 13 | 2,4-D acid | 27.94 | 16.91 | 60.5 |
| | Florasulam | 0.28 | 0.20 | 71.4 |
| | Fluroxypyr-meptyl | 4.10 | 4.01 | 97.8 |

What is claimed:

1. A method to provide a stable emulsifiable concentrate composition containing a mixture of a free acid of a carboxylic acid herbicide and an ester of a different carboxylic acid herbicide by hindering de-esterification and transesterification which comprises incorporating into the composition from about 10 to about 600 grams/liter (g/L) of an N,N-dimethyl ($C_6$-$C_{12}$)alkyl amide or an N—($C_5$-$C_{11}$)alkanoyl morpholine.

2. A method to provide a stable emulsifiable concentrate composition containing a triazolopyrimidine herbicide having at least one methoxy group on the triazolopyrimidine ring in admixture with a free acid of a carboxylic acid herbicide and/or an ester of a carboxylic acid herbicide by hindering degradation of the methoxy group to an hydroxy group which comprises incorporating into the composition from about 10 to about 600 g/L of an N,N-dimethyl ($C_6$-$C_{12}$)alkyl amide or an N—($C_5$-$C_{11}$)alkanoyl morpholine.

3. The method of claim 1 or 2 in which the carboxylic acid herbicide is 2,4-D, MCPA, dicamba, clopyralid, fluoroxypyr or triclopyr.

4. The method of claim 1 or 2 in which the N,N-dimethyl ($C_6$-$C_{12}$)alkyl amide is mixture of N,N-dimethyloctanamide/decanamide.

5. The method of claim 2 in which the triazolopyrimidine herbicide having at least one methoxy group on the triazolopyrimidine ring is florasulam.

6. A stable emulsifiable concentrate composition comprising a) from about 5 to about 500 g/L of a carboxylic acid herbicide as a free acid, b) from about 10 to about 700 g/L of a different carboxylic acid herbicide as an ester, c) from about 10 to about 600 g/L of an N,N-dimethyl ($C_6$-$C_{12}$)alkyl amide or an N—($C_5$-$C_{11}$)alkanoyl morpholine, and d) from about 60 to about 720 g/L of an organic solvent and surfactants.

7. A stable emulsifiable concentrate composition comprising a) from about 1 to about 5 g/L of a triazolopyrimidine herbicide having at least one methoxy group on the triazolopyrimidine ring, b) from about 5 to about 700 g/L of a carboxylic acid herbicide as a free acid and/or an ester of a carboxylic acid herbicide, c) from about 10 to about 600 g/L of an N,N-dimethyl ($C_6$-$C_{12}$)alkyl amide or an N—($C_5$-$C_{11}$)alkanoyl morpholine, and d) from about 60 to about 720 g/L of an organic solvent and surfactants.

8. The composition of claim 6 or 7 in which the carboxylic acid herbicide is 2,4-D, MCPA, dicamba, clopyralid, fluoroxypyr or triclopyr.

9. The composition of claim 6 or 7 in which the N,N-dimethyl ($C_6$-$C_{12}$)alkyl amide is mixture of N,N-dimethyloctanamide/decanamide.

10. The composition of claim 7 in which the triazolopyrimidine herbicide having at least one methoxy group on the triazolopyrimidine ring is florasulam.

\* \* \* \* \*